(12) United States Patent
Arrington et al.

(10) Patent No.: US 11,311,232 B2
(45) Date of Patent: Apr. 26, 2022

(54) SYSTEMS AND METHODS FOR MANAGING SLEEP DISORDERS

(71) Applicant: Beacon Sleep Solutions, Salt Lake City, UT (US)

(72) Inventors: Joseph B. Arrington, Salt Lake City, UT (US); Mica N. Sloan, Salt Lake City, UT (US); Pace H. Cranney, Salt Lake City, UT (US)

(73) Assignee: Beacon Sleep Solutions, Tooele, UT (US)

( * ) Notice: Subject to any disclaimer, the term of this patent is extended or adjusted under 35 U.S.C. 154(b) by 463 days.

(21) Appl. No.: 16/254,419

(22) Filed: Jan. 22, 2019

(65) Prior Publication Data
US 2019/0223781 A1    Jul. 25, 2019

Related U.S. Application Data

(63) Continuation-in-part of application No. 15/876,137, filed on Jan. 20, 2018, now abandoned.

(51) Int. Cl.
| | |
|---|---|
| *A61B 5/00* | (2006.01) |
| *A61B 5/0205* | (2006.01) |
| *A61M 21/00* | (2006.01) |
| *A61B 5/11* | (2006.01) |
| *A61B 5/024* | (2006.01) |

(52) U.S. Cl.
CPC .......... *A61B 5/4815* (2013.01); *A61B 5/0022* (2013.01); *A61B 5/0205* (2013.01); *A61B 5/486* (2013.01); *A61B 5/4809* (2013.01); *A61B 5/681* (2013.01); *A61B 5/7455* (2013.01); *A61B 5/024* (2013.01); *A61B 5/11* (2013.01); *A61B 5/4836* (2013.01); *A61M 2021/0022* (2013.01);
(Continued)

(58) Field of Classification Search
CPC ..... A61B 5/4815; A61B 5/4809; A61B 5/024; A61B 5/4836; A61B 5/11; A61B 5/7455; A61B 5/681; A61B 5/486; A61B 5/0022; A61M 2021/0022; A61M 2021/0027; A61M 2021/0044
See application file for complete search history.

(56) References Cited

U.S. PATENT DOCUMENTS

| | | | |
|---|---|---|---|
| 2002/0128540 A1* | 9/2002 | Kim ...................... | A61B 5/486 600/301 |
| 2014/0135612 A1* | 5/2014 | Yuen ..................... | A61B 5/112 600/407 |

(Continued)

*Primary Examiner* — Samuel G Gilbert
(74) *Attorney, Agent, or Firm* — Bryant J. Keller; Kirton McConkie

(57) ABSTRACT

Some implementations of the present invention relate to systems and methods for managing disruptive sleep disorders. In some cases the described systems and methods may detect an episode of parasomnia, such as sleep paralysis, sleepwalking, night terrors, chronic nightmares, sleep hallucinations, sleeping disorders associated with post-traumatic stress disorder, or a similar sleep disturbance, and provide a stimulus to wake the user from the episode of parasomnia. Accordingly, in some cases, the present invention comprises a sensor to monitor a user's physiological indicators to first determine if the user is asleep and then identify the onset of an episode of parasomnia, and a mechanism for providing a sensory stimulus to wake the user. Other implementations are also described.

20 Claims, 9 Drawing Sheets

(52) U.S. Cl.
CPC .............. *A61M 2021/0027* (2013.01); *A61M 2021/0044* (2013.01)

(56) References Cited

U.S. PATENT DOCUMENTS

2015/0174362 A1* 6/2015 Panova ................. A61M 21/02
                                                        600/27
2016/0262690 A1* 9/2016 Chen .................... A61B 5/4815
2016/0302718 A1* 10/2016 Laura LaPoint ...... A61M 21/02

* cited by examiner

SYSTEMS AND METHODS FOR MANAGING SLEEP DISORDERS

BACKGROUND OF THE INVENTION

Related Applications

This is a non-provisional utility patent application that claims priority to U.S. Provisional patent application Ser. No. 15/876,137, filed on Jan. 20, 2018, and entitled "SLEEP PARALYSIS DETECTION DEVICE WITH EXTERNAL STIMULATION"; the entire disclosure of which is incorporated herein by reference.

Field of the Invention

The present invention relates generally to managing disruptive sleep disorders. In particular, some implementations of the present invention relate to systems and methods for monitoring sleep, detecting an episode of parasomnia (and/or any other suitable sleep disorder), such as sleep paralysis, sleepwalking, night terrors, chronic nightmares, sleep hallucinations, sleeping disorders associated with post-traumatic stress disorder, snoring, sleep talking, or a similar sleep disturbance, and providing a stimulus to wake a user from the episode of parasomnia. In some such implementations, the present invention comprises one or more (a) sensors to monitor one or more of a user's physiological indicators to first determine if the user is asleep and then to identify the onset of an episode of parasomnia (and/or any other set identifier), and (b) mechanisms for providing a sensory stimulus to wake the user.

Background and Related Art

Sleep plays a vital role in good health and well-being. Yet, many individuals struggle with disruptive sleep disorders that negatively impact their ability to get quality sleep. In general, sleep disorders are deviations from normal sleep patterns that can affect overall health, safety, quality of life, and increase the risk of other health problems.

While there are many different types of sleep disorders, they are commonly grouped into categories based on how they impact sleep. For example, sleep disorders are often diagnosed using their symptoms, including behavioral changes, abnormalities in the natural sleep-wake cycle, difficulty falling asleep, difficulty staying asleep, difficulty waking up, experiencing abnormalities during sleep, and breathing problems. In this regard, sleep disorders are commonly classified as: insomnias, hypersomnias, parasomnias, sleep-related breathing disorders, circadian rhythm sleep-wake disorders, and sleep-related movement disorders (e.g., restless legs syndrome).

Sleep disorders are believed to have a variety of different causes, which may include physical problems, other underlying medical problems (e.g., post-traumatic stress disorder), psychiatric problems, genetics, medications, and natural aging.

As indicated above, parasomnias are one of the many categories of sleep disorders. Parasomnias are often characterized by abnormal events that occur during sleep. These abnormal events may include undesirable behaviors, dreams, emotions, movements, or perceptions that occur during or in association with sleep.

Episodes of parasomnia often occur in association with specific stages of sleep or sleep-wake transitions. In this regard, it is common to divide parasomnias into two categories: parasomnias that occur during arousal from rapid eye movement ("REM") sleep and parasomnias that occur during arousal from non-rapid eye movement ("NREM") sleep. Non-REM parasomnias often include sleep terrors/night terrors, sleepwalking (i.e., somnambulism), confusional arousals, while REM parasomnias often include nightmares, sleep paralysis, and REM sleep behavior disorder.

Sleep paralysis is one specific parasomnia that is frequently manifested when an individual suffering from the disorder endures the undesirable experience of being fully conscious, but is unable to move their body. Many have reported episodes of sleep paralysis lasting anywhere between thirty seconds to 20 minutes or more.

It is believed that sleep paralysis occurs when a person passes between stages of wakefulness and sleep. In particular, healthy individuals move through three different stages while they sleep. Before entering REM sleep, chemicals are released that paralyze the body, save for the eyes and breathing muscles, to prevent sleepers from acting out their dreams. Sleep paralysis commonly occurs when the sleeper's brain wakes up during REM sleep. Fear and disorientation can often set in while the chemicals responsible for dreams create vivid hallucinations, which may cause the individual to panic.

Like many other sleep disorders, individuals experiencing sleep paralysis may become exhausted from these stressful episodes and from struggling to regain control of their body. Moreover, those who suffer from frequent episodes often develop anxiety about falling asleep.

Although sleep is critical for proper brain function and productivity, current methods and devices for treating disruptive sleep disorders are not necessarily without their shortcomings. By way of example, medications are commonly used to treat sleep disorders. Although medications may be helpful in reducing the occurrences of sleep disorder episodes or the symptoms of the disorder, they are often habit forming and may not assist an individual that is experiencing a sleep disorder episode. Moreover, medications may be cost prohibitive and require frequent meetings with a prescribing physician furthering reducing their widespread accessibility.

In another example, behavior therapy may be used to manage sleep disorders. Behavior therapy helps to identify and replace thoughts and behaviors that may cause sleep problems with habits that promote sound sleep. However, behavior therapy may require significant time for the individual to learn the new habits, which are not always effective. Behavior therapy can also have accessibility problems because the referral system may limit access to physician specialists. Additionally, the time and cost to meet with a physician specialist to develop new habits may be cost prohibitive.

In another example, sleep monitoring devices have been developed to collect data regarding an individual's sleeping patterns. However, these sleep monitoring devices only monitor sleep with little or no direction for how to use the information. While these devices may be helpful in diagnosing a sleep disorder, they provide no immediate assistance to an individual that is experiencing a sleep disorder episode.

Thus, while techniques currently exist that are used to treat disruptive sleep disorders, challenges still exist, including those discussed above. Accordingly, it would be an improvement in the art to augment or even replace current techniques with other techniques.

SUMMARY OF THE INVENTION

The present invention relates generally to managing disruptive sleep disorders. In particular, some implementations of the present invention relate to systems and methods for monitoring sleep, detecting an episode of parasomnia (and/or any other suitable sleep disorder), such as sleep paralysis, sleepwalking, night terrors, chronic nightmares, sleep hallucinations, sleeping disorders associated with post-traumatic stress disorder, and/or a similar sleep disturbance, and providing one or more stimuli to wake the user (e.g., from the episode of parasomnia). In some such implementations, the present invention comprises one or more sensors to monitor a user's physiological indicators to determine if the user is asleep and/or to identify the onset of an episode of parasomnia, and a mechanism for providing a sensory stimulus to wake the user.

In some implementations, the present invention includes a sleep disorder management device comprising one or more sensors, sensory stimulators, housings, and/or connectors that are configured to adjustably maintain contact (e.g., direct or otherwise) between the sleep disorder management device and the user.

With general reference to the sleep disorder management device, the device may be used to monitor a user's sleeping patterns (and/or status) to determine if the user is undergoing a sleep disorder episode and then deliver one or more stimuli (e.g., physically perceivable stimuli) to end the sleep disorder episode (and/or to wake the user). In some implementations, the sleep disorder management device is triggered by a continued, constant, and/or significant deviation from the user's (and/or one or more preset) normal sleeping patterns. In this regard, some implementations of the device can be effective in treating a variety of different sleep disorders where a sleep disorder episode is distinguishable from a user's normal sleeping patterns and where a stimulus would assist the user in returning to their normal sleeping pattern and/or waking from their sleep disorder episode. Some examples of sleep disorders that could be managed by the device include, but are not limited to, insomnias, hypersomnias, parasomnias, sleep-related breathing disorders, circadian rhythm sleep-wake disorders, and/or sleep-related movement disorders.

In at least some implementations, the sleep disorder management device can be deployed for use at virtually any chosen location on the user's body. In particular, in some non-limiting examples, the device can be placed on the user's head, neck, arm, wrist, hand, chest, stomach, back, leg, ankle, foot, and/or other location for detecting and intervening in a sleep disorder episode. In this regard, some examples of device configurations include, but are not limited to, watches, bracelets, bands, straps, hats, headgear, necklaces, patches, adhesives, wearables, clothing articles, and/or any other article that is convenient, safe to wear, and/or will not affect the normal sleeping routine of users.

With reference to the sensor, the sensor can comprise virtually any suitable instrument that can detect, read, and/or otherwise monitor the sleeping patterns and/or status of the user. In this regard, the sensor may be used to identify when the user is awake, experiencing a normal sleeping pattern, and/or experiencing a sleep disorder episode.

In some implementations, one or more sensors measure the biometric and/or physiological signals of the user to identify when the user is awake, experiencing a normal sleeping pattern, and/or experiencing a sleep disorder episode. In other implementations, the sensor measures the vital signs of the user to identify when the user is awake, experiencing a normal sleeping pattern, and/or experiencing a sleep disorder episode. In yet other implementations, the sensor measures movement of the user to identify when the user is awake, experiencing a normal sleeping pattern, and/or experiencing a sleep disorder episode With reference to the sensory stimulator, the sensory stimulator may comprise virtually any suitable device or devices for providing an intervening sensory stimulation during a sleep disorder episode to assist the user in returning to their normal sleeping pattern and/or waking from their sleep disorder episode. Some examples of suitable sensory stimulators include, but are not limited to, one or more speakers, buzzers, and/or other devices that are configured to provide an auditory alert, vibrators to provide a haptic alert, light producing devices to provide a visual alert, heating and/or cooling mechanisms to provide a temperature alert, smell, and/or any other suitable device or devices for providing one or more sensory alerts to the user. In this regard, in some particular implementations, the sensory stimulator comprises an electric motor with an unbalanced mass on its driveshaft to produce perceptible vibrations.

In some implementations, the sensory stimulator will continue until: the user returns to their normal sleeping pattern, wakes from their sleep disorder episode and deactivates the sensory stimulator, and/or any other suitable condition is met. In some implementations, the sensory stimulator will increase in frequency and/or strength until the user returns to their normal sleeping pattern, wakes from their sleep disorder episode, and/or another suitable condition is met.

With reference to the housing, some implementations of the housing are designed to receive the sensor and the sensory stimulator, while maintaining contact between the sensor and the user's skin. In this regard, the housing may be constructed of any suitable material, including, without limitation, from a rigid material. In some other embodiments, however, the housing comprising a material that is flexible and that has one or more other structural characteristics that allow it to be placed in static compression with the user's skin.

With reference to the connector, the connector may comprise virtually any suitable means or mechanism of securing the housing to the user to maintain contact between the sensor and the use (e.g., the user's skin). Some examples of suitable connectors include, but are not limited to, one or more bands, straps, adhesives, stickers, ties, clasps, cords, clips, clamps, crimps, pins, magnets, hooks, loops, hook and loop fasteners, ratchets, buckles, snaps, buttons, clothing articles, belts, and/or any other suitable component or components that are configured to allow the connector to be selectively attached to the user.

Thus, in at least some implementations, the present invention comprises a wearable sleep disorder management device that resembles a watch with a band that maintains contact between the sensor and the user's wrist. In some implementations, the present invention further comprises a vibrator (and/or any other suitable stimulator) that is activated when the sensor detects a deviation from the user's normal (and/or from a set) sleeping pattern.

By using at least some implementations of the present invention, a user can effectively manage their sleep disorder. In some implementations, the present invention will detect one or more inputs from the user (e.g., one or more biometric signals, physiological signals, vital signs, sounds, talking, and/or movements). In some implementations, the present invention will transduce the input into an interpretable form (e.g., using an internal computer device). In some implementations, the present invention will include preset baseline parameters (e.g., awake parameters, NREM parameters, and/or REM parameters). In some implementations, the present invention will interpret the input from the user to determine the user's specific baseline parameters (e.g., awake parameters, NREM parameters, and/or REM parameters from the user and/or set in any other suitable manner). In some implementations, the present invention will determine whether the user is asleep (e.g., by comparing the input from the user to the baseline parameters). In some implementations, the present invention will determine whether the user is experiencing a sleep disorder episode (e.g., by comparing the input from the user to the baseline parameters). In some implementations, the present invention will provide a sensory feedback to the user if the user is determined to be experiencing a sleep disorder episode (e.g., haptic feedback, vibrations, auditory alerts, visual alerts, a change in temperature, a shock, an olfactory alert, and/or any other suitable form of stimulus). Thus, in at least some implementations, the present invention assists the user in returning to their normal sleeping pattern and/or waking from their sleep disorder episode.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter. As such, this summary is provided to introduce a selection of concepts in a simplified form and is not intended to identify key feature or essential features of the claimed subject matter.

BRIEF DESCRIPTION OF THE DRAWINGS

In order that the manner in which the above-recited and other features and advantages of the present invention are obtained, a more particular description of the invention will be rendered by reference to specific embodiments thereof, which are illustrated in the appended drawings. Understanding that the drawings are not necessarily drawn to scale or in proper proportion, and that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

Embodiments of the invention will now be described more fully hereinafter with reference to the accompanying drawings, which are intended to be read in conjunction with the summary, the detailed description, and any preferred and/or particular embodiments, examples, and variations specifically discussed or otherwise disclosed. This invention may, however, be embodied in many different forms and should not be construed as being limited to the embodiments set forth herein; rather, these embodiments are provided by way of illustration only and so that this disclosure will be thorough, complete, and fully convey the full scope of the invention to those skilled in the art.

The following disclosure of the present invention is grouped into two subheadings, namely "Systems and Methods for Managing Sleep Disorders" and "Representative Operating Environment." The utilization of the subheadings is for convenience of the reader only and is not to be construed as limiting in any sense.

Systems and Methods for Managing Sleep Disorders

As mentioned, the present invention relates generally to managing one or more sleep disorders. In particular, some implementations of the present invention relate to systems and methods for monitoring sleep, detecting an episode of parasomnia (and/or any other sleep disorder, and/or triggering event), such as sleep paralysis, sleepwalking, night terrors, chronic nightmares, sleep hallucinations, sleeping disorders associated with post-traumatic stress disorder, and/or any other suitable sleep disturbance, and providing one or more stimuli to at least partially wake the user from (and/or otherwise help the use come out of) the episode of parasomnia (and/or any other sleep disorder). In some such implementations, the present invention comprises one or more sensors to monitor one or more of a user's physiological indicators to first determine if the user is asleep and then (in some cases) to identify the onset of an episode of parasomnia (and/or another sleep disorder), and a mechanism for providing one or more sensory stimuli to wake the user.

Figure 1:
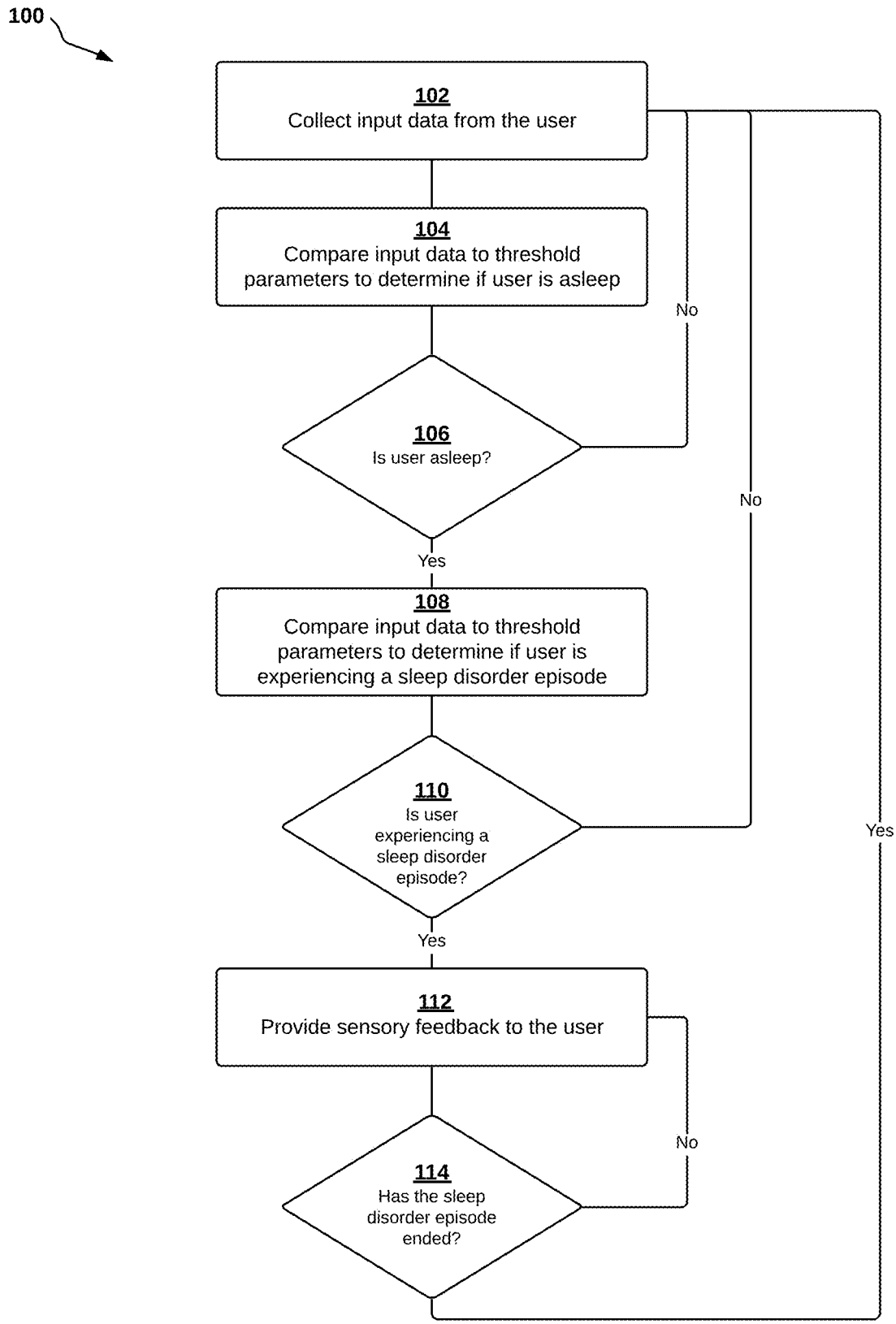
FIG. 1 illustrates a flowchart depicting a method for managing a sleep disorder in accordance with some embodiments.

While the sleep disorder management methods described herein can include any suitable step or any suitable combination of elements in any manner that would allow it to assist a user in managing their sleep disorder, FIG. 1 shows one example of a non-limiting method for managing sleep disorders. In this regard, while all methods described herein can have one or more portions thereof be rearranged, reordered, omitted, replaced, substituted, performed simultaneously, performed separately, repeated, and/or otherwise be modified in any suitable manner, FIG. 1 shows one embodiment where the method 100 comprises: collecting input data from the user (as shown at box 102), comparing the input data to threshold parameters to determine if the user is asleep (as shown at boxes 104 and 106), comparing the input data to threshold parameters to determine if the user is experiencing a sleep disorder episode (as shown at boxes 108 and 110), and providing sensory feedback to the user to end the sleep disorder episode (as show at boxes 112 and 114) if a sleep disorder episode is occurring.

The depicted method 100 may be used to manage any number of undesirable behaviors, dreams, emotions, movements, physiological functions, and/or perceptions that occur during and/or in association with sleep. In this regard, the method 100 may be used to manage a variety of sleep disorders, including, but not limited to, insomnias, hypersomnias, parasomnias, sleep-related breathing disorders, circadian rhythm sleep-wake disorders, and sleep-related movement disorders (e.g., restless legs syndrome).

With respect to box 102, in some embodiments, collecting input data from the user comprises gathering one or more biometric signals, physiological signals, vital signs, user movements, sounds, speech (e.g., sleep talking), and/or any other suitable input data for determining whether the user is awake, the user is sleeping, and/or the user is experiencing a sleep disorder episode. In some particular embodiments, collecting input data from the user (as shown at box 102) comprises utilizing one or more sensors to gather measurable biometric and/or physiological signals, including, but not limited to, heart-beat rate (e.g., electrocardiogram signal or ECG/EKG signal and/or any other suitable identifier identifying a user's heartrate), respiratory rate and content (e.g., capnogram and/or any other suitable respiratory identifier), skin conductance (e.g., electrodermal activity, EDA signal, and/or any other suitable skin conductance identifier), muscle current (e.g., electromyography, EMG signal, and/or any other suitable muscle current identifier), brain electrical activity (e.g., electroencephalography, EEG signal, and/or any other suitable brain activity identifier), eye movements (e.g., electrooculography, EOG signal, and/or other eye movement identifier), sound, talking, and/or any other suitable biometric and/or physiological signals. In other particular embodiments, collecting input data from the user (as shown at box 102) comprises utilizing a sensor to gather measurable vital signs of the user, including, but not limited to, body temperature, pulse rate, respiration rate, blood pressure, oxygen content, perspiration, and/or any other suitable vital sign. In yet other particular embodiments, collecting input data from the user (as shown at box 102) comprises utilizing one or more sensors to gather measurable movement of the user, including, but not limited, pedometers, accelerometers, GPS, gyroscopes, moisture sensors, sweat sensors, and/or any other suitable device used to measure movement of the user.

Indeed, in some embodiments, the collecting input data from the user (as shown at box 102) comprises utilizing a sensor to determine the user's heart-beat rate, which varies depending on whether the user is awake (e.g., variable), asleep (e.g., depressed), in one or more stages of sleep, and/or experiencing a sleep disorder episode (e.g., elevated). In some embodiments, the heart rate is variable. Accordingly, in some embodiments, the sensor is configured to monitor a user's heartrate, which can be variable even when a user is asleep, awake, and/or in any other suitable state.

With respect to box 104, in some embodiments, the input data collected from the user (e.g., biometric signals, physiological signals, vital signs, user movements, and/or any other suitable input) is compared to one or more identified threshold values to determine if the user is asleep. In this regard, the specific value of the user input data may fluctuate depending on whether the user is awake or asleep. It should be understood that, in some embodiments, determining whether the user is asleep is optionally a prerequisite to determining that the user is experiencing a sleep disorder episode. This initial determination may allow the method 100 to be performed on the user throughout the day (e.g., when the user is awake and asleep), while preventing normal activities that occur while the user is awake from being interpreted as a sleep disorder episode.

In some embodiments, the comparison of input data from the user to threshold parameters (as shown at box 104) utilize default parameters that may not be set or adjusted by the user. In some embodiments, the comparison of input data from the user to threshold parameters (as shown at box 104) utilizes custom parameters that may be manually set or adjusted by the user.

In some embodiments, if the input data collected from the user exceeds a known threshold, the user is determined to be sleeping (as shown at box 106). In other embodiments, if the input data collected from the user falls below a known threshold, the user is determined to be sleeping (as shown at box 106).

With respect to box 108, in some embodiments, the input data collected from the user (e.g., biometric signals, physiological signals, vital signs, user movements, and/or other input) is compared to a known threshold value to determine if the user is experiencing a sleep disorder episode. In this regard, the specific value of the user input data may fluctuate depending on whether the user experiencing normal sleeping patterns or experiencing a sleeping disorder episode.

In some embodiments, the comparison of input data from the user to threshold parameters (as shown at box 108) utilize default parameters that may not be set or adjusted by the user. In some embodiments, the comparison of input data from the user to threshold parameters (as shown at box 108) utilizes custom parameters that may be manually set or adjusted by the user. In some embodiments, if the input data collected from the user exceeds a known threshold, the user is determined to be experiencing a sleep disorder episode (as shown at box 110). In other embodiments, if the input data collected from the user falls below a known threshold, the user is determined to be experiencing a sleep disorder episode (as shown at box 110). In still other embodiments, if the input data collected from the user falls within a known threshold range, the user is determined to be experiencing a sleep disorder episode (as shown at box 110).

With respect to box 112, in some embodiments, a sensory feedback is provided to the user to wake the user and/or assist the user in returning to a normal sleep pattern. In this regard, providing a sensory feedback to the user (as shown at box 112) comprises delivering any suitable stimulus that provides an intervening stimulation during a sleep disorder episode to assist the user in returning to their normal sleeping pattern and/or waking from their sleep disorder episode. Some examples of suitable stimuli include, but are not limited to, auditory alerts, haptic alerts, visual alerts, temperature alerts, electrical shocks, smells, and/or any other suitable intervening stimulation.

In some embodiments, as depicted in box 114, the sensory stimulator will continue until the user returns to their normal sleeping pattern, wakes from their sleep disorder episode, and/or one or more other desired parameters are met. In some embodiments, the sensory stimulator will increase in frequency and/or strength until the user returns to their normal sleeping pattern and/or wakes from their sleep disorder episode.

In the depicted embodiment, the method 100 is performed continuously by repeatedly collecting input data from the user (as shown at box 102) until it is determined that the user is asleep (as shown at box 106) and the user is experiencing a sleep disorder episode (as shown at box 110).

Figure 2:
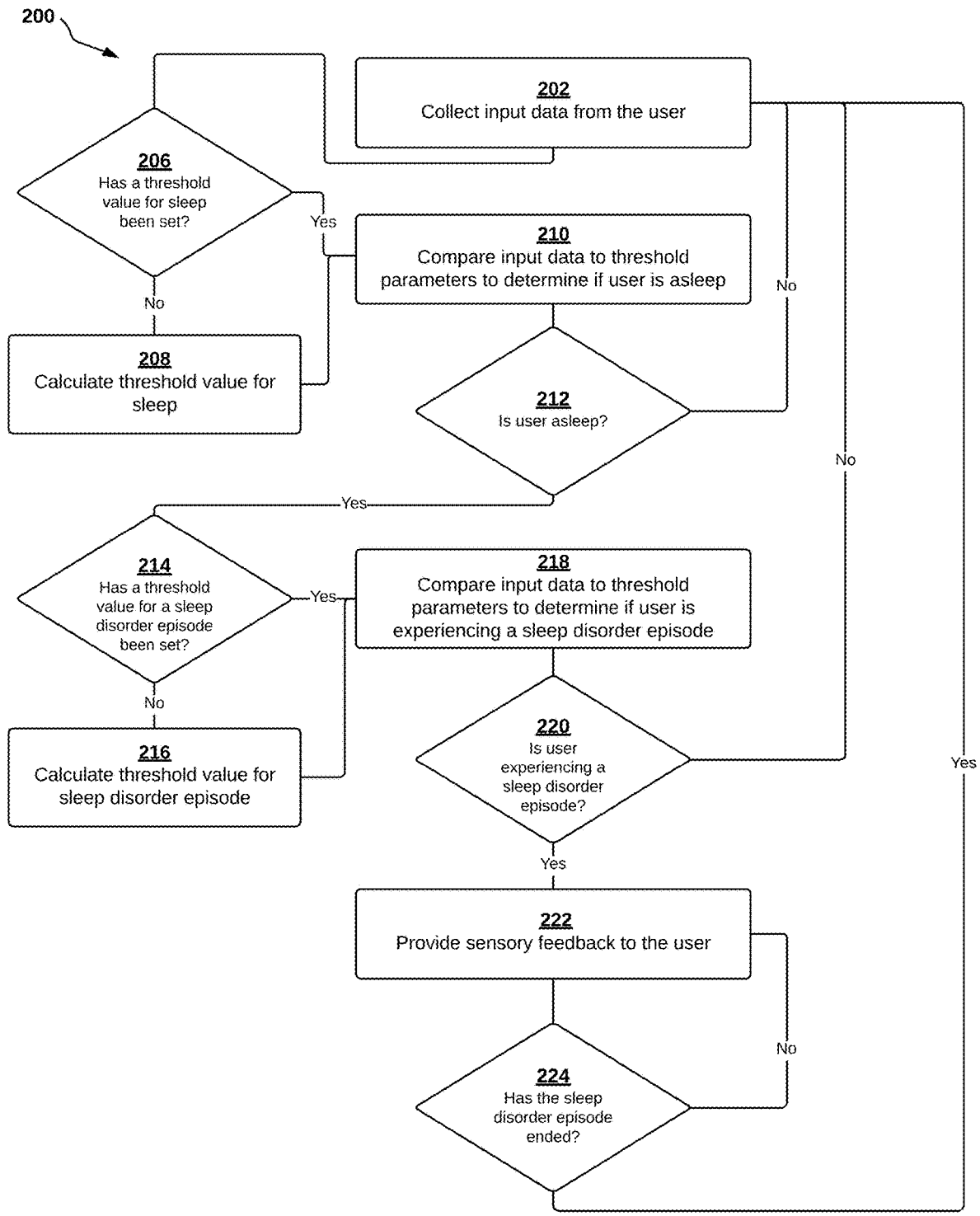
FIG. 2 illustrates a flowchart depicting a method for managing a sleep disorder, where the methods determines the user's threshold parameters in accordance with some embodiments.

With respect to FIG. 2, some embodiments of the sleep disorder management methods 200 described herein further comprise one or more methods for determining the threshold values to recognize when a user transitions from being awake to asleep. In this regard, in some embodiments, such thresholds are gathered based on input from many users, medical staff, machine learning, and/or in any other suitable manner. Indeed, in some embodiments, the methods 200 "learn" the threshold for identifying whether a user is asleep or wake (boxes 206 and 208) (e.g., through algorithms, computer learning, etc.). In some such embodiments, the method calculate the threshold parameter through iteration with the use and/or others.

In some embodiments, the sleep disorder management methods 200 described herein further comprise a method for determining the threshold values to identify when a user transitions from experiencing normal sleeping patterns to experiencing sleep disorder episodes (boxes 214 and 216). In this regard, in some embodiments, the methods 200 "learn" the threshold for determining whether the user is experiencing a normal sleep pattern or experiencing a sleep disorder episode (boxes 218 and 220) (e.g., through algorithms, computer learning, etc.). In some such embodiments, the method calculates the threshold parameter through iteration.

Figure 3A:
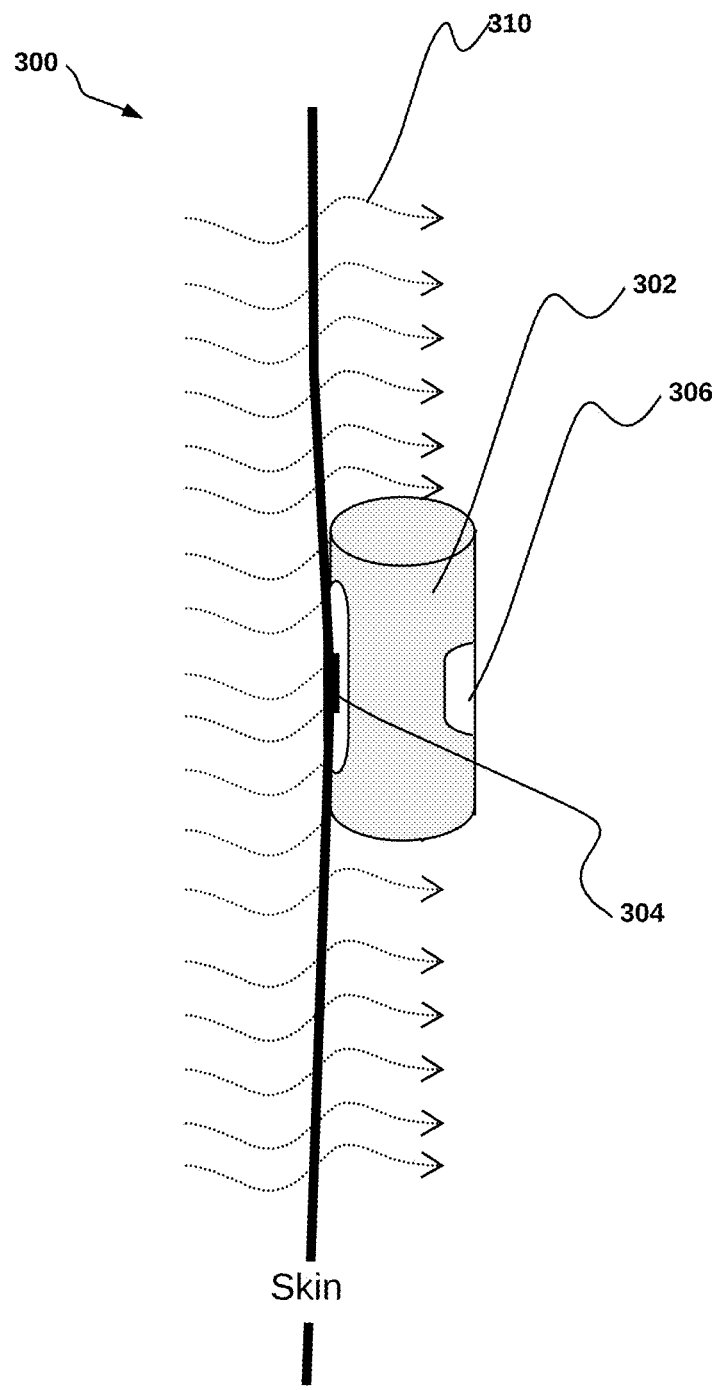
FIG. 3A illustrates a side perspective view of a sleep disorder management device comprising a sensor and a sensory stimulator in accordance with some embodiments.
Figure 3B:
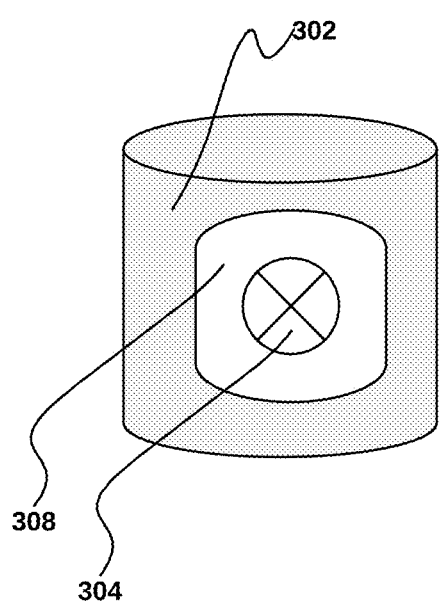
FIG. 3B illustrates a side perspective view of a sleep disorder management device comprising a sensor and a sensory stimulator in accordance with some embodiments.

While the sleep disorder management devices described herein can include any suitable feature that allow them to identify when a user is experiencing a sleep disorder episode and intervene in the sleep disorder episode, FIGS. 3A-3B show that, in some embodiments, the described sleep disorder management device 300 comprises one or more housings 302, sensors 304, sensory stimulators 306, and/or connectors 308.

In the embodiments depicted in FIGS. 3A-3B, the housing 302 is sized to receive the sensor 304 and the sensory stimulator 306, while maintaining the relative position of the sensor 304 and the sensory stimulator 306 with respect to each other. These embodiments also depict a connector 310 to maintain selective contact between the sensor 304 (placed on or in the housing 302) and the user (e.g., the user's skin). In this regard, static compression between the sensor 304 and the skin allows the sleep disorder management device 300 to monitor the user's biometric signals, physiological signals, vital signs, user movements, and/or any other measurable indicator that emanates from the user's body (e.g., as illustrated by the arrows labeled as 310).

With general reference to the sleep disorder management device 300, the device may be used to monitor a user's sleeping patterns to determine if the user is undergoing a sleep disorder episode and then deliver a physical stimulus to remedy the sleep disorder episode. In some implementations, the sleep disorder management device 300 is triggered by a continued, constant, and/or significant deviation from the user's normal sleeping patterns (e.g., by analyzing the measurable indicators that emanate from the user's body). In this regard, the device may be effective in treating a variety of different sleep disorders where a sleep disorder episode is distinguishable from a user's normal sleeping patterns and a stimulus may assist the user in returning to their normal sleeping pattern and/or waking from their sleep disorder episode. Some non-limiting examples of sleep disorders that could be managed by the device 300 include, but are not limited to, insomnias, hypersomnias, parasomnias, sleep-related breathing disorders, circadian rhythm sleep-wake disorders, and any other suitable sleep-related disorders.

It should be understood that the sleep disorder management device 300 may have any suitable size or shape for convenient and effective application on the user's body. Indeed, in some embodiments, the sleep disorder management device 300 has a shape that is partially cuboidal, partially square, partially rectangular, spherical, elliptical, rounded, curved, polygonal, symmetrical, asymmetrical, irregular, and/or any other suitable shape or combination of shapes. Moreover, in some embodiments, instead of comprising a suitably shaped object having more of a two dimensional appearance, the sleep disorder management device 300 comprises one or more balls, cubes, pyramids, prisms, and/or any other suitably shaped object or objects having more of a three dimensional appearance.

By way of non-limiting example, some embodiments of the sleep disorder management device 300 substantially resemble and/or be incorporated in an armband, a baseball cap, a band, a beanie, a belt, a bracelet, a buckle, a cap, a cuff, a collar, earmuffs, glasses, gloves, a hat, a headset, a jacket, neckwear, pajamas, patches, a ring, slippers, a shirt, shoes, shorts, underclothes, a visor, a watch, a wrist clasp, and/or any other suitable article of clothing or wearable device that may be worn during the day and while sleeping.

Thus, in at least some embodiments, the sleep disorder management device 300 is deployed for use at virtually any chosen location on the user's body. In particular, in some non-limiting examples, the device can be placed on the user's head, neck, arm, wrist, hand, chest, stomach, back, leg, ankle, foot, and/or other location for detecting and intervening in a sleep disorder episode (e.g., by analyzing the measurable indicators that emanate from the user's body).

With regard to the housing 302, in some embodiments the housing 302 can comprise any suitable object that is configured to hold the sensor 304, the sensory stimulator 306, and/or any other internal components of the sleep disorder management device 300 (e.g., computer devices, processors, batteries, memory, input and output ports, solar cells, and/or any other suitable component). In some embodiments, the housing 302 is configured to conform to the user's body to maximize contact between the sensor 304 and the user's skin. In this regard, the housing 302 may comprise any suitable material configured to hold the sensor 304 and/or the sensory stimulator 306 in place, while conforming to the user's body to maximize conform. In some not limiting examples, the housing 302 comprises natural, woven, non-woven, knitted, netting, synthetic, and/or technical fabrics or materials; leathers; bamboo based materials; polymers; ceramics; rubbers; woods; metals; or any other suitable material or combination of suitable materials. Indeed, in some embodiments, the housing 302 comprises one or more fabrics, plush fabrics, cloths, terry cloths, felts, plush felts, velour plush fabrics, long hair plush fabrics, velvets, furs, leathers, microfibers, polyester, rayon, cotton wool, linen, faux fur, plush furs, plastics, polymers, metals, ceramics, and/or any other suitable material. In some cases, for instance, the housing 302 comprises a bonded polymer substance or silicone material to maximize flexibility.

With regard to the sensor 304, the sensor 304 can comprise virtually any suitable instrument that can detect, read, and/or otherwise can be used to monitor the sleeping patterns (and/or any other applicable information) of the user. In this regard, the sensor may be used to gather measurable data to determine when the user is awake, experiencing a normal sleeping pattern, or experiencing a sleep disorder episode (e.g., by analyzing the measurable indicators that emanate from the user's body). Specifically, a user experiencing a sleep disorder episode may have an increased heart-beat rate, increased blood pressure, skin conductance (e.g., from increased perspiration), and/or increased breathing rate. Conversely, breathing rate, oxygen levels, blood pressure, and movement may be depresses when transitions from being awake to asleep.

In some embodiments, the sensor 304 measures the biometric and/or physiological signals of the user. Some examples of measurable biometric and/or physiological signals, include, but are not limited to, heart-beat rate (e.g., electrocardiogram signal or ECG/EKG signal), respiratory rate and content (e.g., capnogram), skin conductance (e.g., electrodermal activity or EDA signal), muscle current (e.g., electromyography or EMG signal), brain electrical activity (e.g., electroencephalography or EEG signal), eye movements (e.g., electrooculography or EOG signal), speech, sounds, snoring, apnea, hypopnea, and/or any other suitable biometric and/or physiological signals.

In other embodiments, the sensor 304 measures the vital signs of the user. Some examples of measurable vital signs included, but are not limited to, body temperature, pulse rate, respiration rate, blood pressure, perspiration, oxygen content, and/or any other suitable vital signs.

In yet other embodiments, the sensor 304 measures movement of the user. Some examples of sensors that can measure movement and/or sounds of the user include, but are not limited to, pedometers, accelerometers, gyroscopes, GPS, microphones, moisture sensors, conductivity sensors, and/or any other suit suitable mechanical and/or electromechanical device used to measure movement.

In some cases, for instance, the sensor 304 comprises a heart-beat rate monitor to determine whether the user is awake, asleep, and/or experiencing a sleep disorder episode. In such examples, the sensor 304 may be used to determine when the user is experiencing normal sleep patterns (e.g., uniform heart-beat rate) or experiencing a distressing sleep disorder experience, such as sleep paralysis or night terrors (e.g., elevated heart-beat rate). In other cases, for instance, the sensor 304 comprises an accelerometer to determine whether the user is awake, asleep, and/or experiencing a sleep disorder episode. In such examples, the sensor 304 may be used to determine when the user is experiencing normal sleep patterns (e.g., no movement) or experiencing a distressing sleep disorder experience, such as sleepwalking (e.g., movement).

In some embodiments, the sleep disorder management device 300 comprises multiple sensors 304 to determine whether the user is awake, asleep, experiencing a sleep disorder episode, and/or to gather any other suitable information. In one such example, a first sensor 304 (e.g., an accelerometer) may be used to determine when the user is awake or asleep, while a second sensor 304 may be used to determine whether the user is experiencing a distressing sleep disorder experience (e.g., an electro-dermal activity monitor).

With regard to the sensory stimulator 306, the sensory stimulator 306 may comprise virtually any suitable stimulator that provides one or more intervening stimulations during a sleep disorder episode to assist the user in returning to their normal sleeping pattern, waking from their sleep disorder episode, and/or to achieve any other suitable criteria. Some examples of suitable sensory stimulators 306 include, but are not limited to, one or more speakers to provide an auditory alert, vibrators to provide a haptic alert, displays and/or light producing devices to provide a visual alert, heating and/or cooling mechanisms to provide a temperature alert, smell, and/or any other suitable device for providing a sensor alert.

In this regard, in some particular implementations the sensory stimulator 306 comprises an electric motor with an unbalanced mass on its driveshaft to produce perceptible vibrations. In some implementations, the sensory stimulator 306 will continue until the user returns to their normal sleeping pattern, wakes from their sleep disorder episode, and/or until any other suitable criterion is met. In some implementations, the sensory stimulator 306 will increase in frequency and/or strength until the user returns to their normal sleeping pattern and/or wakes from their sleep disorder episode.

With reference to the connector 308, the connector 308 may comprise virtually any suitable means of securing the housing to the user to maintain contact between the sensor and the user's skin. Some examples of connectors 308 include, but are not limited to, one or more belts, bands, straps, adhesives, stickers, ties, clasps, cords, clips, clamps, crimps, pins, magnets, hooks, loops, hook and loop fasteners, buckles, snaps, buttons, clothing articles, and/or any other suitable component or components that are configured to allow the device to be selectively attached to the user. In some such examples, as depicted in FIG. 3B, the connector 308 resembles an adhesive pad. In other such examples, the connector 308 resembles a wristwatch band.

The connector can comprise any suitable material that allows it to function as described herein. Indeed, some implementations of the connector 308 comprise natural, woven, non-woven, knitted, netting, synthetic, and/or technical fabrics or materials; leathers; bamboo based materials; polymers; ceramics; rubbers; woods; metals; or any other suitable material or combination of suitable materials. Indeed, in some embodiments, the connector comprises one or more fabrics, plush fabrics, cloths, terry cloths, felts, plush felts, velour plush fabrics, long hair plush fabrics, velvets, furs, leathers, microfibers, polyester, rayon, cotton wool, linen, faux fur, plush furs, plastics, polymers, metals, ceramics, and/or any other suitable material.

Figure 4:
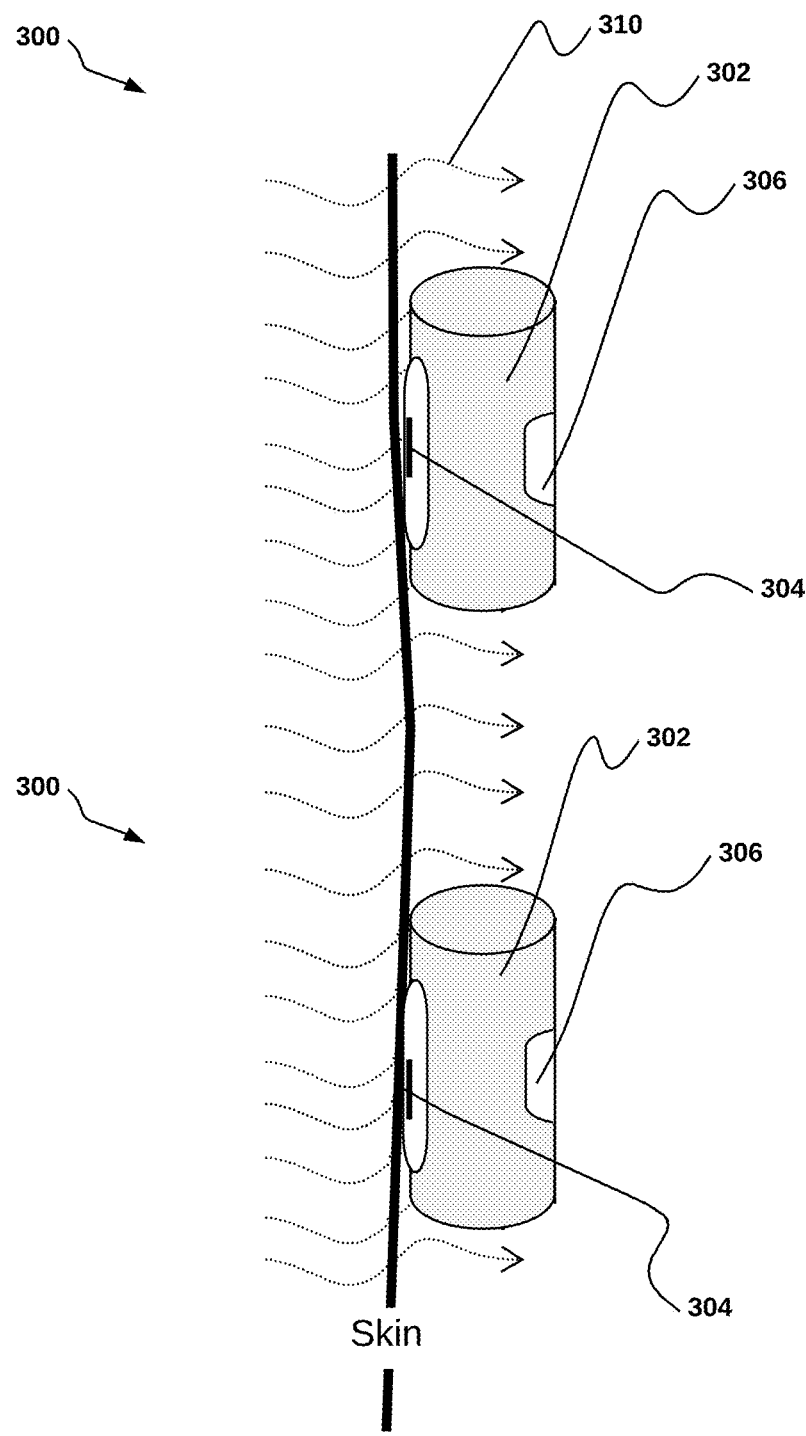
FIG. 4 illustrates a side perspective view of a plurality of a sleep disorder management devices each comprising a sensor and a sensory stimulator in accordance with some embodiments.

Although FIGS. 3A-3B only depict a single sleep disorder management device 300, it should be understood, as depicted in FIG. 4, that multiple sleep disorder management device 300 may be placed on a single user and/or in locations on the user. In such embodiments, a plurality of sleep disorder management devices 300 may be helpful in gathering the measurable indicators that emanate from the user's body (e.g., as illustrated by the arrows labeled as 310). In other such embodiments, a plurality of sleep disorder management devices 300 may be helpful in providing an intervening stimulation during a sleep disorder episode to assist the user in returning to their normal sleeping pattern and/or waking from their sleep disorder episode.

In this regard, each sleep disorder management device 300 may be placed on a location on the user's body to maximize the efficacy of the sensor 304 and/or the sensory stimulator 306. In other such embodiments, a plurality of sleep disorder management devices 300 may be helpful in maximizing efficacy by providing redundancy.

Figure 5:
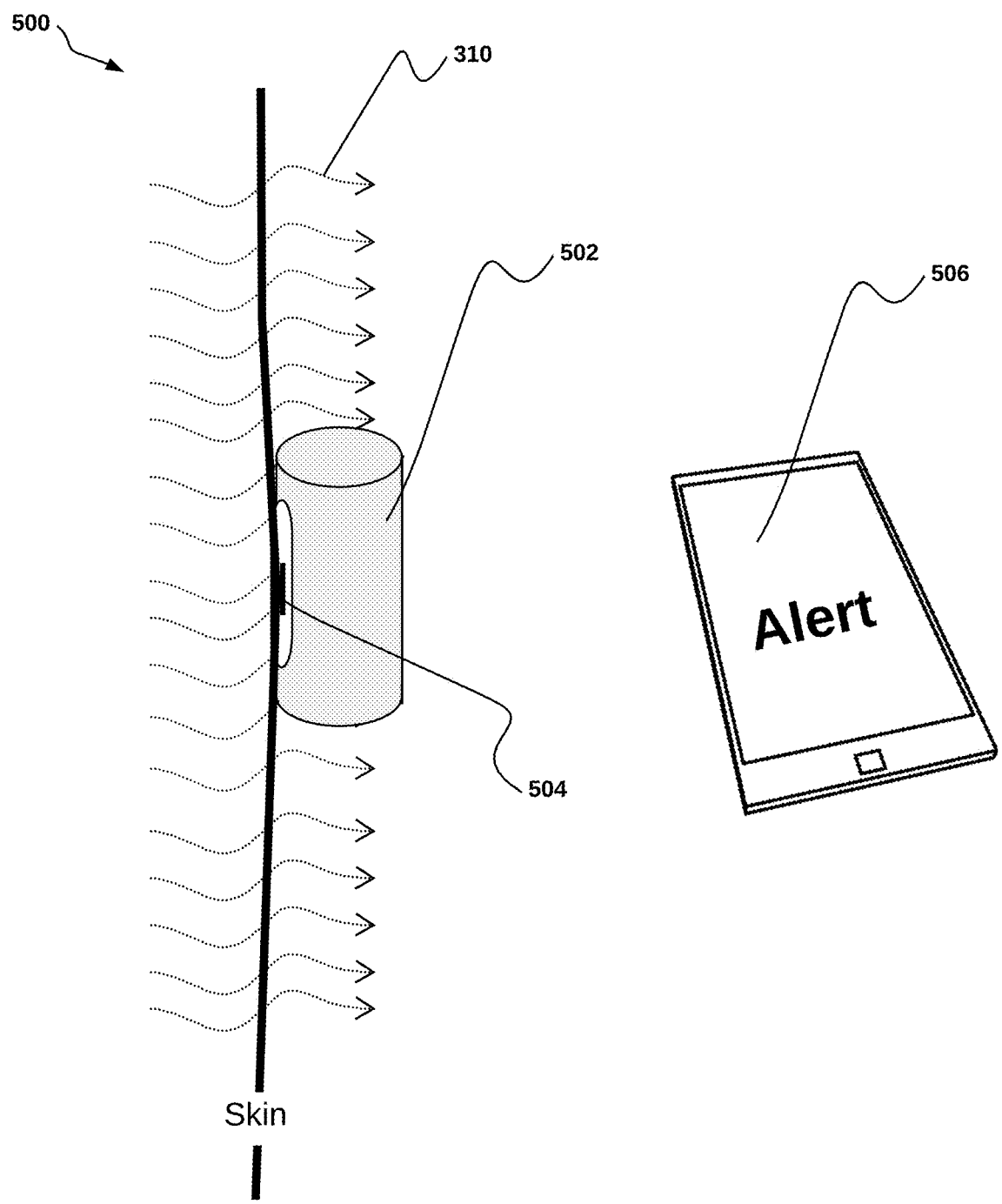
FIG. 5 illustrates a sleep disorder management device comprising a sensor that is separated from the sensory stimulator in accordance with some embodiments.

Similarly, it should also be understood, as depicted in FIG. 5, that the housing 502 may not always comprise the sensor 504, the sensory stimulator 506, and/or the other internal components of the sleep disorder management device 500 (e.g., computer devices, processors, batteries, memory, input and output ports, etc.). As depicted in FIG. 5, in some embodiments, the housing 502 comprises the sensor 504, but not the sensory stimulator 506.

In this regard, the sensory stimulator 506 may be incorporated in a remote device. Specifically, in some embodiments, separating the sensor 504 and the sensory stimulator 506 may allow the sensor 504 to be placed at a location on the body to maximize its efficacy, while the sensory stimulator 506 may be placed at or near a location on the body to maximize its efficacy.

In other embodiments, the sleep disorder management device 500 incorporates an additional third-party device to utilize and/or integrate its sensory stimulator 506. Some non-limiting examples of third-party devices include one or more alarm clocks, lights, thermostats, doorbells, smartphones, tablets, speakers, smart bands, and/or any similar device containing a sensory stimulator 506.

In some such examples, the sleep disorder management device 500 utilizes wireless protocols, including, but not limited to, Bluetooth, NFC, Wi-Fi, LiFi, 3G, infrared, and/or any other suitable means for establishing wireless communication between the sensor 504 and the sensory stimulator 506. In other such examples, the sleep disorder management device 500 comprises a hardwired connection for establishing communication between the sensor 504 and the sensory stimulator 506, including, but not limited to, Ethernet cable, lightning cable, thunderbolt cable, micro-USB cable, USB-C cable, and/or any other suitable cable for establishing communication between the sensor 504 and the sensory stimulator 506.

Figure 6A:
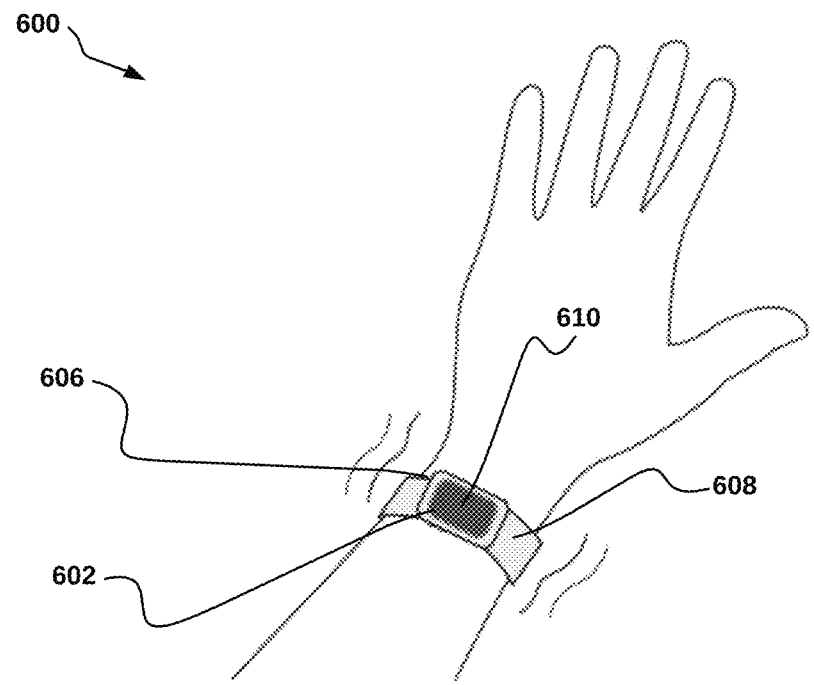
FIG. 6A illustrates a top perspective view of a sleep disorder management device that is configured to resemble a smartwatch in accordance with some embodiments.
Figure 6B:
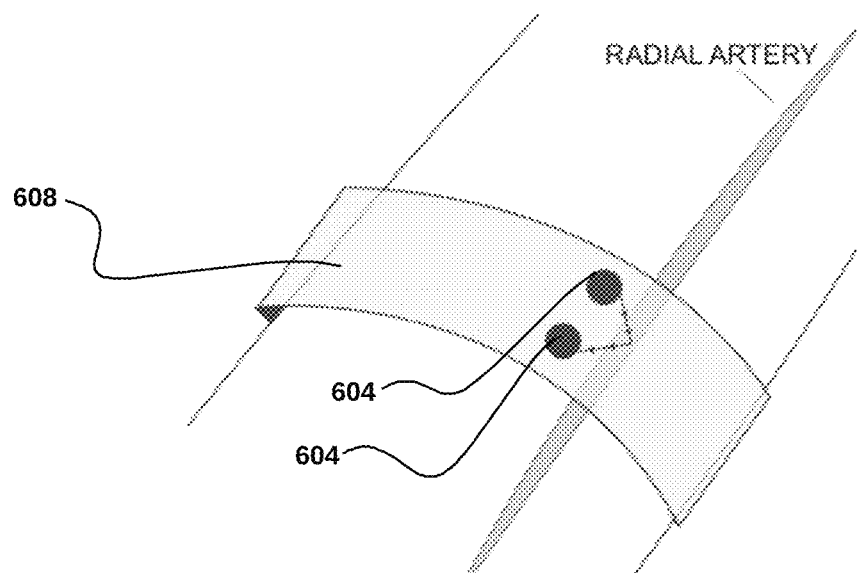
FIG. 6B illustrates a bottom perspective view of a sleep disorder management device that is configured to resemble a smartwatch in accordance with some embodiments.

FIGS. 6-7 depict particular embodiments of the sleep disorder management device 600, 700 that resemble a watch. With regard to the sleep disorder management device depicted in FIGS. 6A-6B, in some embodiments, the sleep disorder management device 600 comprises a flexible housing 602, a heart-rate beat sensor 604 (e.g., an optical LED light source and an LED light sensor), a vibrator 606 built in the flexible housing 602, a wristband 608, and a display screen 610 to provide a graphic user interface to interact with the sleep disorder management device 600. In this regard, the sleep disorder management device 600 may utilize the heart-rate beat sensor 604 to read the user's heart-beat rate (e.g., from the radial artery, as depicted in FIG. 6B) to identify when the user is experiencing a sleep disorder episode (such as a paralytic event) and then intervene to wake the user.

In particular, in some embodiments, the sleep disorder management device 600 monitors the user's heart-beat rate and wakes the user when there is an abnormal heart-beat rate, which is often indicative of the fear responses detected during the sleep disorder episodes. More specifically, in some embodiments, the sleep disorder management device 600 triggers the vibrator 606 after detecting continued, constant, and significant deviation from the user's typical REM sleep heart-beat rate ranges.

In such embodiments, the placement of the sleep disorder management device 600 on the user's wrist allows the vibrator 606 to shake the user's arm to send an afferent signal that breaks the sleep signal cycle (and/or that performs any other suitable function). In this regard, some embodiments of the sleep disorder management device 600 are configured to continue to increase the intensity of the vibrator 606 until the user wakes up (and/or another criterion is met). In these embodiments, the vibrator 606 mimics the physical interactions that have been shown anecdotally to wake those experiencing a sleep disorder episode.

With regard to the display screen 610, the display screen 610 may comprise a graphical user interface that allows the user to interact with the sleep disorder management device 600 through graphical icons and visual indicators. In some embodiments, the display screen 610 is configured to be used to notify the user when the sleep disorder management device 600 is properly placed. In other embodiments, the display screen 610 is configured to be used to display the battery status for the device. In yet other embodiments, the display screen 610 may indicate when charging is occurring.

Figure 7A:
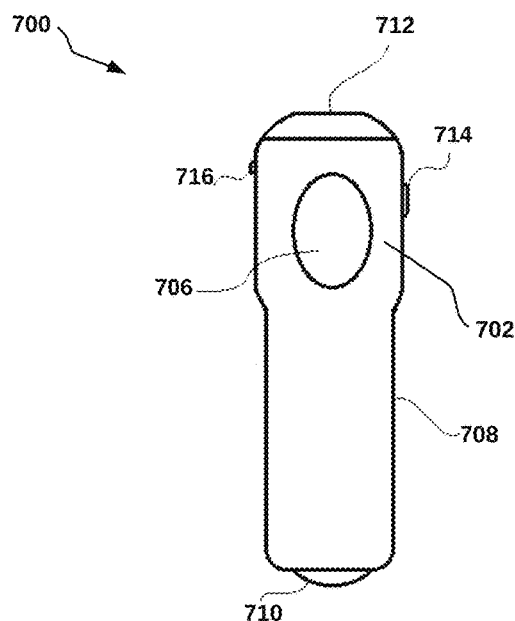
FIG. 7A illustrates a first side perspective view of a sleep disorder management device that is configured to resemble a wrist band in accordance with some embodiments.
Figure 7B:
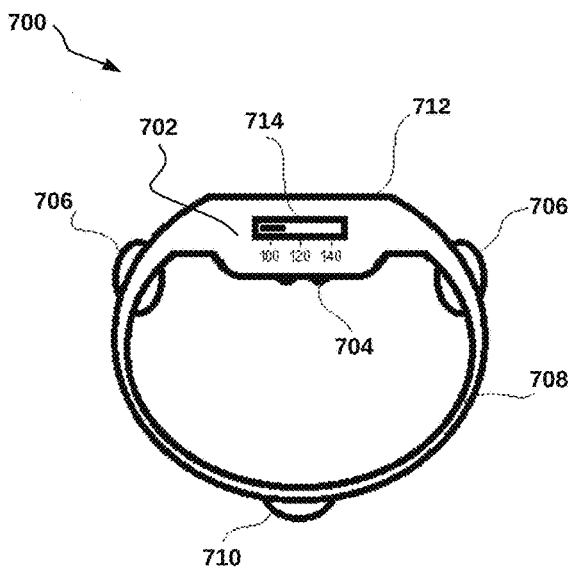
FIG. 7B illustrates a second side perspective view of a sleep disorder management device that is configured to resemble a wrist band in accordance with some embodiments.
Figure 7C:
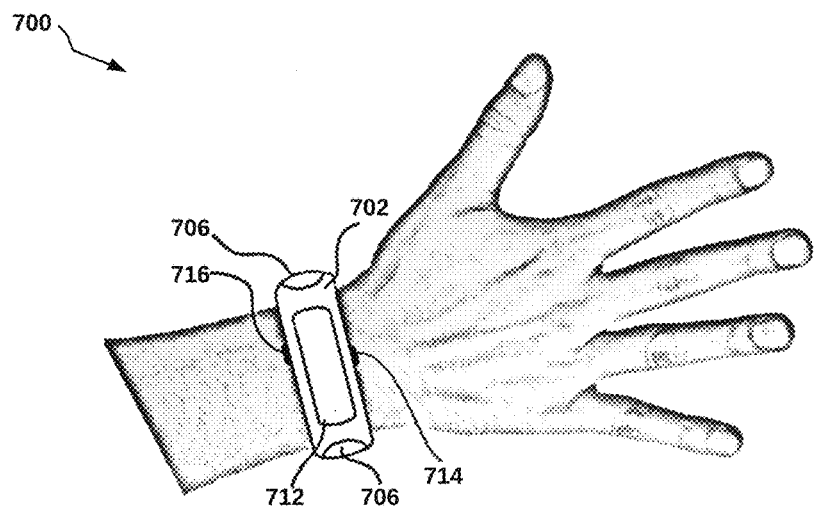
FIG. 7C illustrates a top perspective view of a sleep disorder management device that is configured to resemble a wrist band in accordance with some embodiments.

With regard to the sleep disorder management device 700 depicted in FIGS. 7A-7C, in some embodiments, the sleep disorder management device 700 comprises a housing 702, a heart-rate beat sensor 704 (e.g., an optical LED light source and an LED light sensor), a vibrator 706, a band 708, a clasp 710, a display screen 712 to provide a graphic user interface with the sleep disorder management device 700, a parameter adjustment switch 714, and an wired port 716.

In some such embodiments, the vibrator 706 comprises a plurality of rumble packs. In this regard, a first rumble pack may be configured to be placed over the ulna of the user and a second may be configured to be placed over the radius of the user. In some specific embodiments, the vibrator 706 comprises an electric motor with an unbalanced mass on its driveshaft to produce perceptible vibrations.

In other such embodiments, the parameter adjustment switch 714 may be utilized to adjust the threshold for activating the vibrator 706 (e.g., requisite threshold for any measurable indicator that emanates from the user's body). In this regard, the parameter adjustment switch 714 may provide a plurality of different thresholds (e.g., heart-beat rates) that the user can select to maximize the efficacy of the sleep disorder management device 700. In some such embodiments, the parameter adjustment switch 714 may provide a spectrum of thresholds that, if met, will activate the vibrator 706. Although FIGS. 7A-7C depict a physical switch, it should be understood that a virtual switch and/or a digital switch may be implemented.

In some embodiments, the wired port 716 may be utilized to charge one or more internal batteries of the sleep disorder management device 700. In other embodiments, the wired port 716 may be utilized to transfer data to or from the sleep disorder management device 700.

Representative Operating Environment

The systems and methods for managing sleep disorders can be used with or in any suitable operating environment and/or software. In this regard, FIGS. 8-9 and the corresponding discussion are intended to provide a general description of a suitable operating environment (e.g., computer system) in accordance with some embodiments of the described systems and methods. As will be further discussed below, some embodiments embrace the use of one or more processing (including, without limitation, micro-processing) units in a variety of customizable enterprise configurations, including in a networked configuration, which may also include any suitable cloud-based service, such as a platform as a service or software as a service.

Some embodiments of the described systems and methods embrace one or more computer readable media, wherein each medium may be configured to include or includes thereon data or computer executable instructions for manipulating data. The computer executable instructions include data structures, objects, programs, routines, or other program modules that may be accessed by one or more processors, such as one associated with a general-purpose processing unit capable of performing various different functions or one associated with a special-purpose processing unit capable of performing a limited number of functions. In this regard, in some embodiments, the processing unit comprises a specialized processing unit (e.g., a transducing processing unit, graphics processing unit, or otherwise) that is configured for detecting and managing sleeping disorders. In still other embodiments, the processing unit comprises a general processing unit. In any case, computer executable instructions cause the one or more processors of the enterprise to perform a particular function or group of functions and are examples of program code means for implementing steps for methods of processing. Furthermore, a particular sequence of the executable instructions provides an example of corresponding acts that may be used to implement such steps.

Examples of computer readable media (including non-transitory computer readable media) include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing unit.

Figure 8:
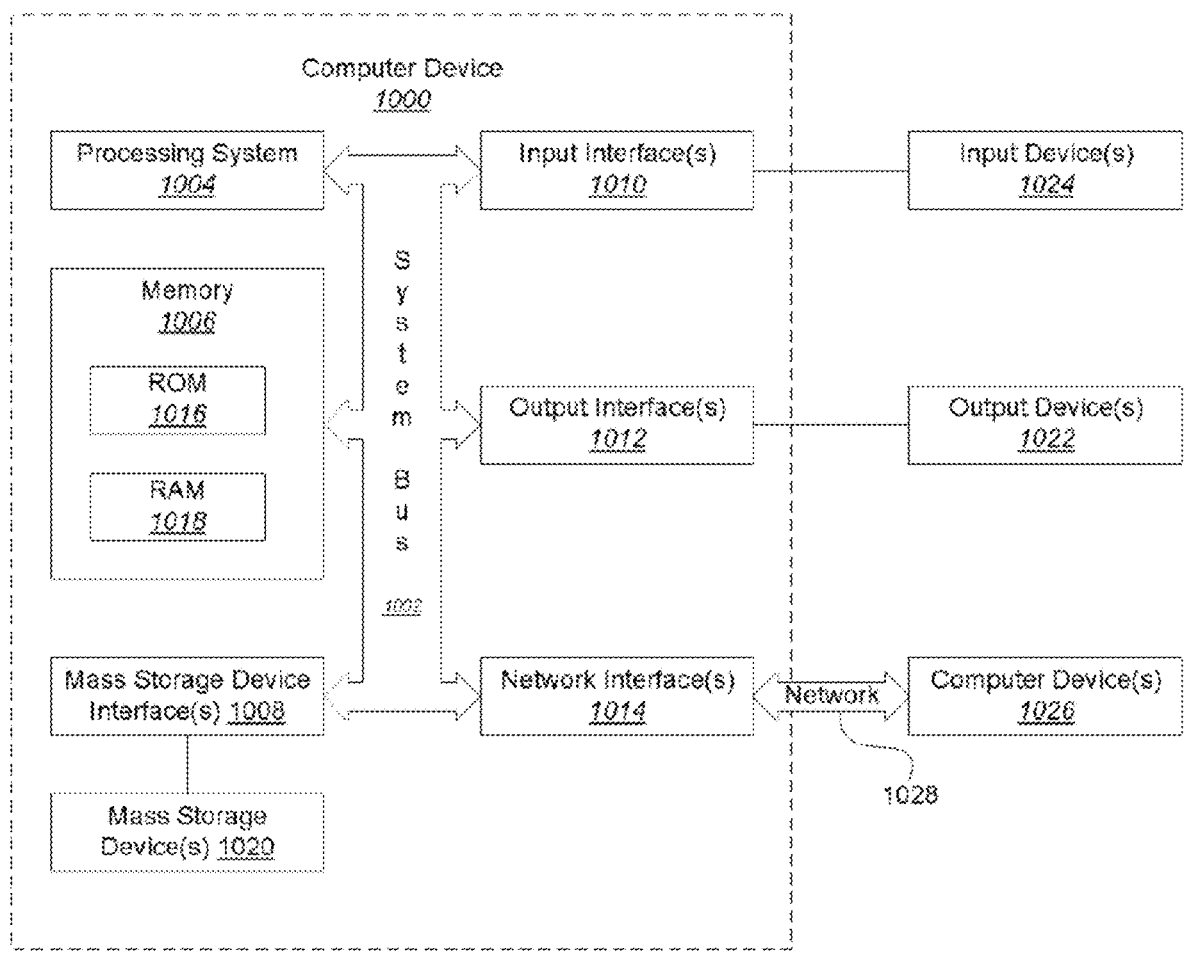
FIG. 8 illustrates a representative computer system environment in which some embodiments of the invention may be practiced.

With reference to FIG. 8, a representative system includes computer device 1000 (e.g., a unit capable of importing the user data from the sensor and exporting a command to activate a sensory stimulator), which may be a general-purpose or special-purpose computer (e.g., processing unit). For example, computer device 1000 may be a personal computer, a notebook computer, a PDA or other hand-held device, a workstation, a minicomputer, a mainframe, a supercomputer, a multi-processor system, a network computer, a processor-based consumer device, a cellular phone, a tablet computer, a smart phone, a smartwatch, a feature phone, a smart appliance or device, a control system, or the like. In some embodiments, computer device 1000 is a specialized computer (e.g., a unit capable of importing the user data from the sensor and exporting a command to activate a sensory stimulator and/or any other suitable specialized computer). In some particular embodiments, computer device 1000 is a specialized computer for importing the user data from the sensor, interpreting the user data, and porting a command to activate a sensory stimulator.

Computer device 1000 includes system bus 1002, which may be configured to connect various components thereof and enables data to be exchanged between two or more components. System bus 1002 may include one of a variety of bus structures including a memory bus or memory controller, a peripheral bus, or a local bus that uses any of a variety of bus architectures. Typical components connected by system bus 1002 include processing system 1004 and memory 1006. Other components may include one or more mass storage device interfaces 1008, input interfaces 1010, output interfaces 1012, and/or network interfaces 1014, each of which will be discussed below. In some embodiments, the systems and methods for managing sleep disorders may synergistically improve the operation of efficiency of the computer device 1000.

Processing system 1004 includes one or more processors, such as a central processor and optionally one or more other processors designed to perform a particular function or task. It is typically processing system 1004 that executes the instructions provided on computer readable media, such as on the memory 1006, a magnetic hard disk, a removable magnetic disk, a magnetic cassette, an optical disk, or from a communication connection, which may also be viewed as a computer readable medium.

Memory 1006 includes one or more computer readable media (including, without limitation, non-transitory computer readable media) that may be configured to include or includes thereon data or instructions for manipulating data, and may be accessed by processing system 1004 through system bus 1002. Memory 1006 may include, for example, ROM 1016, used to permanently store information, and/or RAM 1018, used to temporarily store information. ROM 1016 may include a basic input/output system ("BIOS") having one or more routines that are used to establish communication, such as during start-up of computer device 1000. RAM 1018 may include one or more program modules, such as one or more operating systems, application programs, and/or program data.

One or more mass storage device interfaces 1008 may be used to connect one or more mass storage devices 1020 to the system bus 1002. The mass storage devices 1020 may be incorporated into or may be peripheral to the computer device 1000 and allow the computer device 1000 to retain large amounts of data. Optionally, one or more of the mass storage devices 1020 may be removable from computer device 1000. Examples of mass storage devices include hard disk drives, magnetic disk drives, tape drives, solid state mass storage, and optical disk drives.

Examples of solid state mass storage include flash cards and memory sticks. A mass storage device 1020 may read from and/or write to a magnetic hard disk, a removable magnetic disk, a magnetic cassette, an optical disk, or another computer readable medium. Mass storage devices 1020 and their corresponding computer readable media provide nonvolatile storage of data and/or executable instructions that may include one or more program modules, such as an operating system, one or more application programs, other program modules, or program data. Such executable instructions are examples of program code means for implementing steps for methods disclosed herein.

One or more input interfaces 1010 may be employed to enable a user to enter data (e.g., initial information or sensor data) and/or instructions to computer device 1000 through one or more corresponding input devices 1022. Examples of such input devices include a keyboard and/or alternate input devices, such as a digital camera, a sensor, bar code scanner, signature and/or writing capture device, pin pad, touch screen, mouse, trackball, light pen, stylus, or other pointing device, a microphone, a joystick, a game pad, a scanner, a camcorder, a copier, a fax machine, and/or other input devices. Similarly, examples of input interfaces 1024 that may be used to connect the input devices 1024 to the system bus 1002 include a serial port, a parallel port, a game port, a universal serial bus ("USB"), a firewire (IEEE 1394), a wireless receiver, a video adapter, an audio adapter, a parallel port, a wireless transmitter, or another interface.

One or more output interfaces 1012 may be employed to connect one or more corresponding output devices 1022 to system bus 1002. Examples of output devices include a sensory stimulatory, a monitor or display screen, a speaker, a wireless transmitter, a printer, and the like. A particular output device 1022 may be integrated with or peripheral to computer device 1000. Examples of output interfaces include a video adapter, an audio adapter, a parallel port, scanner, camera, digital imaging device, imagining sensor and the like.

One or more network interfaces 1014 enable computer device 1000 to exchange information with one or more local or remote computer devices, illustrated as computer devices 1026, via a network 1028 that may include one or more hardwired and/or wireless links. Examples of the network interfaces include a network adapter for connection to a local area network ("LAN") or a modem, a wireless link, or another adapter for connection to a wide area network ("WAN"), such as the Internet. The network interface 1014 may be incorporated with or be peripheral to computer device 1000.

Figure 9:
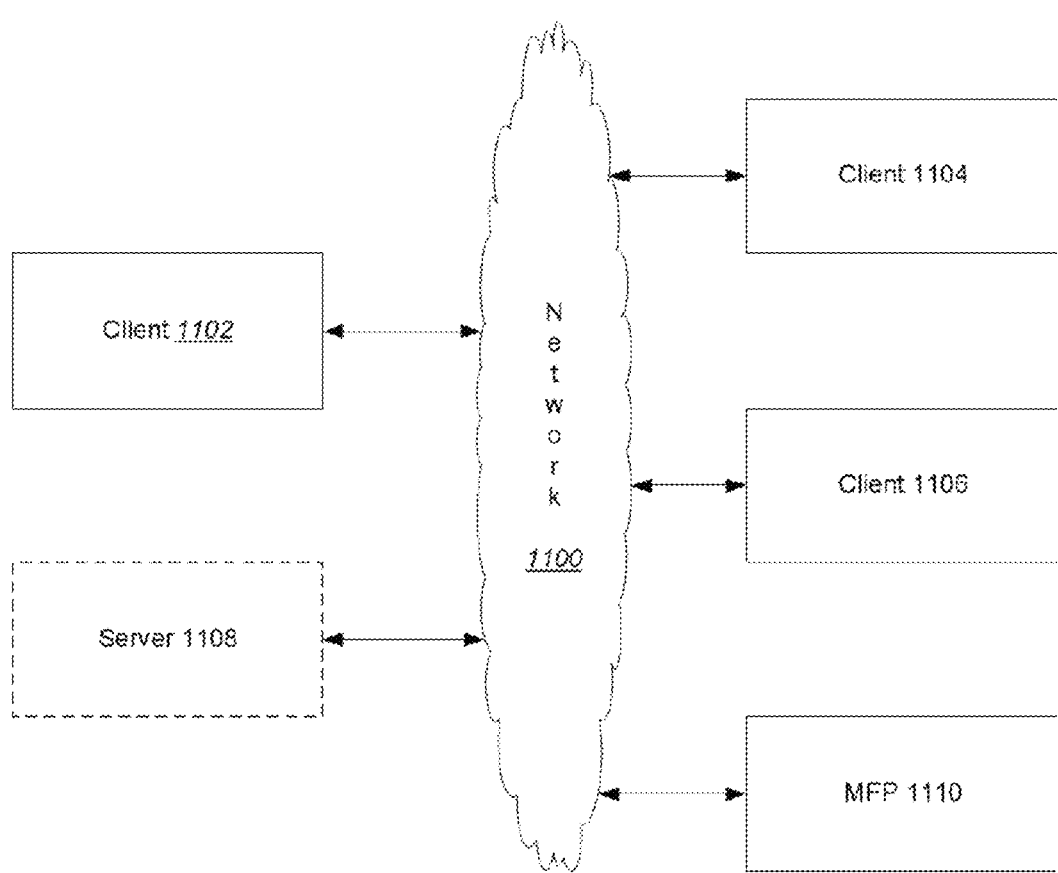
FIG. 9 illustrates a representative networked computer system environment in which some embodiments of the invention may be practiced.

In a networked system, accessible program modules or portions thereof may be stored in a remote memory storage device. Furthermore, in a networked system computer device 1000 may participate in a distributed computing environment, where functions or tasks are performed by a plurality networked computer devices. While those skilled in the art will appreciate that the described systems and methods may be practiced in networked computing environments with many types of computer system configurations, FIG. 9 represents an embodiment of a portion of the described systems in a networked environment that includes clients (1102, 1104, 1106, etc.) connected to a server 1108 via a network 1110. While FIG. 9 illustrates an embodiment that includes 3 clients (e.g., sleep disorder management devices or computers capable of performing sleep disorder management methods) connected to the network, alternative embodiments include at least one client connected to a network or many clients connected to a network. Moreover, embodiments in accordance with the described systems and methods also include a multitude of clients throughout the world connected to a network, where the network is a wide area network, such as the Internet.

Similarly, embodiments of the invention embrace cloud-based architectures where one or more computer functions are performed by remote computer systems and devices at the request of a local computer device. Thus, returning to FIG. 9, the client 1102 may be a computer device having a limited set of hardware and/or software resources. Because the client 1102 is connected to the network 1100, it may be able to access hardware and/or software resources provided across the network 1100 by other computer devices and resources, such as client 1104, client 1106, server 1108, or any other resources. The client 1102 may access these resources through an access program, such as a web browser, and the results of any computer functions or resources may be delivered through the access program to the user of the client 1102. In such configurations, the client 1102 may be any type of computer device or electronic device discussed above or known to the world of cloud computing, including traditional desktop and laptop computers, smart phones and other smart devices, tablet computers, or any other device able to provide access to remote computing resources through an access program such as a browser.

Accordingly, in some embodiments, the described systems and methods can allow for remote management of sleeping disorders (e.g., collecting the user's biometric signals, physiological signals, vital signs, and/or movement data in one or more other locations), monitoring, observation, adjusting, trouble shooting, data collecting, system optimizing, user interaction monitoring, and/or other controlling sleep disorder management devices from many places throughout the world.

In addition to the aforementioned features, the described sleep disorder management device can comprise any other suitable feature, including, without limitation, one or more clocks, screens, ports, sensors, antenna, pedometers, thermometers, gyroscopes, batteries, switches, lights, smart devices, barometers, compasses, accelerometers, and/or any other suitable components.

Accordingly, various embodiments of the invention have many different features, variations and multiple different embodiments. Moreover, the invention has been described in this application at times in terms of specific embodiments for illustrative purposes and without the intent to limit or suggest that the invention conceived is only one particular embodiment. It is to be understood that the invention is not limited to any single specific embodiments or enumerated variations. Many modifications, variations, and other embodiments of the invention will come to mind of those skilled in the art to which this invention pertains, and which are intended to be and are covered by both this disclosure. It is indeed intended that the scope of the invention should be determined by proper interpretation and construction of the disclosure, including equivalents, as understood by those of skill in the art relying upon the complete disclosure at the time of filing.

While the systems and methods of the present invention may be particularly useful for managing sleep disorders, those skilled in the art will appreciate that the described systems and methods can be used in a variety of different applications and in a variety of different fields of use. For instance, the described systems and methods can be used in any application that requires collecting signals and/or inputs from the user, determining the baseline parameters for the signals and/or inputs collected from the user, identifying deviations from baseline parameters for the signals and/or inputs collected from the user, and providing sensory feedback to a facilitate a return of the signals and/or inputs to baseline parameters. Thus, while some implementations of the described systems and methods are used to treat sleep disorders, the described systems and methods can be used to manage a variety of health conditions, including, but not limited to, hypertension, asthma, diabetes, seizures, epilepsy, cancer, stroke, autoimmune disease, sleep apnea, heart attacks, teeth grinding, and/or any other heath condition that requires constant monitoring and sensory feedback to remedy the health condition.

As described herein, the described systems and methods for managing sleep disorders may offer several advantages over certain prior art medications, behavioral therapy, sleep monitors, and/or smartwatches.

In some embodiments, the described systems and methods are readily accessible to users without meeting with a physician. In other embodiments, the described systems and methods are inexpensive, ergonomic, and/or easy to learn or use.

In other embodiments, the described systems and methods are designed to actually interact with a user in a way that is necessary to wake the user.

In yet other embodiments, the described systems and methods utilize a sensory stimulator (e.g., a vibrator) that is stronger that the sensory stimulators (e.g., a vibrator, alarms, etc.) in existing devices. In this regard, the RPMs of the disclosed vibrators may exceed the RPMs in existing devices.

In yet other embodiments, the described systems and methods may detect a measurable indicator that emanates from the user's body, transduce the measurable indicator into interpretable form, interpret the measurable indicator and determine a baseline threshold for the indicator (e.g., both NREM and REM baselines), act upon an abnormal measurable indicator that emanates from the user's body, and/or provide a sensory stimulus sufficient to disrupt a sleep disorder episode.

In yet other embodiments, the described systems and methods will not be affected by normal sleep environment movements. In yet other embodiments, the described systems and methods will not be affected by normal sleep environment movements. In yet other embodiments, the described systems and methods can be utilized throughout the day.

The present invention may be embodied in other specific forms without departing from its spirit or essential characteristics. The described embodiments, examples, and illustrations are to be considered in all respects only as illustrative and not restrictive. The scope of the invention is, therefore, indicated by the appended claims rather than by the foregoing description. All changes that come within the meaning and range of equivalency of the claims are to be embraced within their scope. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., front back, on top of, below, above, top, bottom, side, up, down, under, over, upper, lower, lateral, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

What is claimed is:

1. A method for managing a sleep disorder, the method comprising:
   gathering a physiological indicator from a user;
   using a processor to compare the physiological indicator to a first known parameter to identify whether the user is sleeping;
   using the processor to compare the physiological indicator to a second known parameter to identify if the user is experiencing a sleep disorder episode; and
   providing, via a first vibrator that is placed over a radius bone in an arm of the user and a second vibrator that is placed over an ulna bone in the arm of the user, vibrational sensory feedback to the user when the processor determines that the user is experiencing the sleep disorder episode to end the sleep disorder episode.

2. The method for managing the sleep disorder of claim 1, further comprising:
   increasing the vibrational sensory feedback until the physiological indicator returns to an initial value as determined by the processor based on a reading of a sensor that is gathering the physiological indicator.

3. The method for managing the sleep disorder of claim 1, wherein the physiological indicator is selected from a respiratory rate, a blood oxygen content, a muscle current of the arm, and an audible signal from the user.

4. The method for managing the sleep disorder of claim 1, wherein the gathering the physiological indicator from the user comprises gathering a respiratory rate of the user.

5. The method for managing the sleep disorder of claim 1, wherein the method includes presetting the second known parameter prior to comparing the physiological indicator to the second known parameter.

6. The method for managing the sleep disorder of claim 1, wherein the method includes calculating the second known parameter by monitoring the physiological indicator from the user over a period of time.

7. The method for managing the sleep disorder of claim 1, wherein the physiological indicator is selected from a respiratory rate, a blood oxygen content, a muscle current of the arm of the user.

8. A sleep disorder management device comprising:
   a housing;
   a sensor to collect a biometric signal from a user;
   a processor to analyze the biometric signal and compare the biometric signal to a first parameter and to a second parameter; and
   a sensory stimulator to arouse the user, wherein a comparison between the biometric signal and the first parameter indicates whether the user is asleep and a comparison between the biometric signal and the second parameter identifies whether the user is experiencing a sleep disorder episode, wherein when the processor identifies that the sleep disorder episode is occurring, the processor activates the sensory stimulator, wherein the sensory stimulator comprises a first vibrator that protrudes from the housing and that is configured to be placed over a radius bone of the user when the user wears the sleep disorder management device on an arm of the user, and wherein the sensory stimulator further comprises a second vibrator that protrudes from the housing and that is configured to be placed over an ulna bone of the user when the user wears the sleep disorder management device on the arm of the user.

9. The sleep disorder management device of claim 8, wherein the biometric signal comprises a signal regarding, and wherein the sensor is configured to monitor, at least one of: a respiratory rate, a blood oxygen content, brain electrical activity, muscle current of a portion of the arm, and a respiratory content of the user.

10. The sleep disorder management device of claim 8, wherein the biometric signal comprises a signal relating to a muscle current of a portion of the arm of the user.

11. The sleep disorder management device of claim 8, wherein the biometric signal comprises a signal regarding a respiration rate of the user.

12. The sleep disorder management device of claim 8, wherein the processor is configured to increase an intensity of stimulation provided by the sensory stimulator based on feedback from the sensor indicating a status of the sleep disorder episode.

13. A sleep disorder management device comprising:
a housing comprising a case and a strap;
a first sensor that is configured to monitor a biometric indicator of a user;
a processor to analyze the biometric indicator of the user; and
a sensory stimulator for providing a haptic feedback to the user, wherein the processor identifies if the user is asleep and if the user is experiencing a sleep disorder episode, wherein the sensory stimulator is initiated if the user is asleep and the sleep disorder episode is occurring, wherein the sensory stimulator comprises a first vibrator that protrudes from the housing and that is configured to be placed over a radius bone of the user when the user wears the sleep disorder management device on an arm of the user, and wherein the sensory stimulator further comprises a second vibrator that protrudes from the housing and that is configured to be placed over an ulna bone of the user when the user wears the sleep disorder management device on the arm of the user.

14. The sleep disorder management device of claim 13, wherein the sensory stimulator, once initiated, increases the haptic feedback applied to the user until the sleep disorder episode has ended, as determined by the first sensor.

15. The sleep disorder management device of claim 13, further comprising a second sensor that is configured to identify when the user is walking, wherein the sleep disorder episode comprises sleep walking, and wherein the processor is configured to identify when the user is sleep walking and to initiate the sensory stimulator to the user when the processor identifies that the user is sleep walking.

16. The sleep disorder management device of claim 13, wherein the first vibrator protrudes from the strap on a first side of the case, and wherein the second vibrator protrudes from the strap on a second side of the case, the second side being substantially opposite to the first side.

17. The sleep disorder management device of claim 16, wherein the biometric indicator comprises, and the first sensor is configured to monitor, at least one of: a respiratory rate, a blood oxygen content, and a muscle current of a portion of the arm of the user, and wherein the processor is configured to identify an occurrence of the sleep disorder episode based on information gathered from the first sensor regarding the biometric indicator.

18. The sleep disorder management device of claim 13, wherein the sleep disorder episode comprises a sleep paralysis where the user is conscious and physically paralyzed.

19. The sleep disorder management device of claim 18, wherein the biometric indicator comprises, and the first sensor is configured to monitor, at least one of: an blood oxygen content of the user, and a muscle current of a muscle in the arm of the user, and wherein the processor is configured to identify the sleep disorder episode based on information gathered from the first sensor regarding the biometric indicator of the user.

20. The sleep disorder management device of claim 13, further comprising a pedometer, and wherein the processor is configured to identify when the user is sleep walking.

* * * * *